United States Patent [19]

Heiba

[11] Patent Number: 4,562,279

[45] Date of Patent: Dec. 31, 1985

[54] HERBICIDAL N-SUBSTITUTED-5-(SUBSTITUTED-PHENOXY)-2-SUBSTITUTED BENZOIC ACID SULPHONAMIDES

[76] Inventor: El-Ahmadi I. Heiba, 11 Balsam La., Princeton, N.J. 08540

[21] Appl. No.: 425,429

[22] Filed: Sep. 28, 1982

[51] Int. Cl.[4] ............................................ C07C 143/67
[52] U.S. Cl. ........................................ 560/12; 71/103; 71/100; 260/455 R; 260/455 A; 260/456 A; 549/499
[58] Field of Search .................... 71/103, 100; 560/12; 260/455 R, 455 A, 456 A; 549/499

[56] References Cited

U.S. PATENT DOCUMENTS 3,282,991  11/1966  Klein ..................................... 560/21

FOREIGN PATENT DOCUMENTS 0003416  8/1979  European Pat. Off. .............. 560/21

*Primary Examiner*—Paul J. Killos
*Attorney, Agent, or Firm*—Sixbey, Friedman & Leedom

[57] ABSTRACT

N-sulfenycarbonyl derivatives-5-(substituted-phenoxy)-2-substituted benzoic acid suphonamides, their preparation and use as herbicides are disclosed.

8 Claims, No Drawings

HERBICIDAL N-SUBSTITUTED-5-(SUBSTITUTED-PHENOXY)-2-SUBSTITUTED BENZOIC ACID SULPHONAMIDES

BACKGROUND OF THE INVENTION

Herbicidal 5-(2-chloro-4-trifluoromethyl)-phenoxy-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Patents which describe such compounds and the like include U.S. Pat. Nos. 3,652,645; 3,784,635; 3,873,302; 3,983,168; 3,907,866; 3,798,276; 3,928,416; and 4,063,929. Recent U.S. Pat. No. 4,285,723 which disclose N-sulphonyl-3-phenoxybenzamide derivatives and their salts as herbicides.

SUMMARY OF THE INVENTION

This invention provides certain herbicidal compounds of the formula:

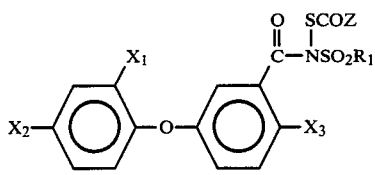

wherein $R_1$ is an alkyl group of 1 to 6 carbon atoms optionally substituted by one or more halogen atoms; phenyl group optionally substituted by one or more halogen atoms; Z is an oxy moiety ($OR_2$); sulfenyl moiety ($SR_2$); $NH_2$; $NHR_2$; $N(R_2)_2$; $R_2CH=N-O$; $(R_2)_2C=N-O$.

Examples of $R_2$ include substituted or unsubstituted phenyl; or substituted or unsubstituted heterocycle, (e.g. having from 5 to 7 rings); $C_1-C_4$alkyl; $C_1-C_4$ alkyl substituted with one or more of phenyl, furfuryl, thiophenyl, Cl, Br, OH, O-alkyl ($C_1-C_4$), SH, S-alkyl, COOH, COO-alkyl, CN, C≡CH, etc.

$X_1$, $X_2$, $X_3$ are substituents capable of imparting herbicidal properties. Suitable substituents include halogen, such as Cl, F and Br, polyhaloalkyl such as $CF_3$, $NO_2$, CN, alkyl, alkoxy, $SO_2$alkyl, $SO_2NH_2$ and COO-alkyl and the like in which the alkyl and alkoxy groups preferably contain 1 to 4 carbon atoms.

Compounds in which $X_1$ is Cl, and $X_2$ is $CF_3$ are preferred. An exemplary compound has the Formula I in which $X_1$ is Cl, $X_2$ is $CF_3$, $X_3$ is $NO_2$, $R_1$ is methyl and $R_2$ is methyl or phenyl. Another exemplary compound with excellent systemic herbicidal activity has the Formula I in which $X_1$ is Cl, $X_2$ is $CF_3$, $X_3$ is $NO_2$, and $R_1$ is methyl and $R_2$ is $CH_2CH_2OH$.

The compounds of this invention can be easily prepared from appropriate precursor by methods known in the art although it is believed that these methods have not previously been applied to make compounds of the present invention. Suitable precursors in which SCOZ of Formula I is hydrogen and salts thereof are known and are described in U.S. Pat. No. 4,285,723, which is incorporated by reference in their entirety. The herinabove precursors can be advantageously prepared in better yields than those reported in U.S. Pat. No. 4,285,723, by reacting the appropriate aryloxyl benzoic acid chloride with substituted sulphonamide $NH_2SO_2R_1$.

The reaction can be conducted by heating the reactants in the temperature ranges 50° C.–200° C., preferably between 110° C.–150° C. The reaction can be affected by heating the mixed reactants per se or in inreactive solvents for example chlorobenzene, toluene and dichlorobenzene and the like. The above mentioned reaction is advantageously conducted in the absence of an acid acceptor.

Compounds of this invention having Formula I can be easily prepared from an intermediate having Formula II.

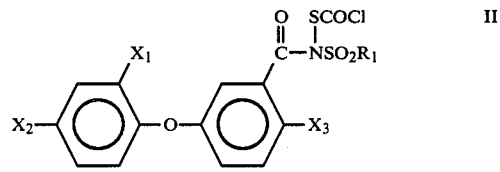

The intermediate having Formula II, can be easily prepared in the known manner and that by reacting at least one mole equivalent of carbonylsulfide dichloride ClSCOCl with the appropriate aryloxyl benzoic acid sulphonamide in its corresponding alkali metal salt form, dispersed or dissolved in inreactive solvent such as, anhydrous tetrahydrofuran, dialkyl ether, dichloromethane and the like. The above described reaction proceeds readily, at room temperature, or lower, and is usually complete in about 1 hour to about 12 hours, but often between about 1 hour to about 6 hours. The overall reaction can be illustrated as:

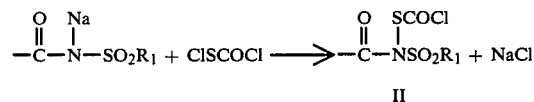

The intermediate having Formula II, need not be separated from the solvent, and can be used as is, without separation from the solvent, for the preparation of compounds of this invention.

Compounds of this invention having Formula I, in which Z is $OR_2$ or $SR_2$ can be easily prepared by reacting the appropriate intermediate of Formula II, synthesized by the procedure described hereinabove, with one mole equivalent of the alkali metal salt of the appropriate alcohol, mercaptan, phenol or thiophenol, etc. The alkali metal salts can be added as anhydrous solids or dispersed or dissolved in inreactive solvent such as tetrahydrofuran, dialkyl ether, dichloromethane and the like. The alkali salt of the appropriate $R_2OH$ or $R_2SH$ can be added to the appropriate intermediate of Formula II, at room temperature, or lower, while stirring. The addition can be completed in about 10 minutes to about one hour but stirring could be continued for an additional one hour to about 6 hours. The solvent is then evaporated and the reaction product can be isolated, purified by crystallization, following simple techniques known to those skilled in the art of organic synthesis. The overall reaction can be illustrated as:

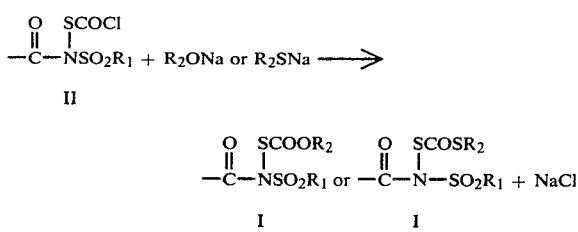

Compounds of this invention having Formula I in which Z is $NH_2$, $NHR_2$ or $N(R_2)_2$ can be easily prepared by reacting the appropriate intermediate II, as synthesized above, with: (a) 2 mole equivalent of $NH_3$ or $NHR_2$ or $N(R_2)_2$, dissolved in inreactive solvent such as tetrahydrofuran, dialkyl ether, dichloromethane and the like, or (b) one mole equivalent of $NH_3$ or $R_2NH_2$ or $(R_2)_2NH$, and an additional one mole equivalent of an acid acceptor such as pyridine or the like. The amine reactant can be added to the intermediate II, over a period of about 30 minutes to about 2 hours, at room temperature, or lower, while stirring. The product can be separated and purified in the manner known to those skilled in the art of organic syntheses.

The over all reaction can be illustrated as:

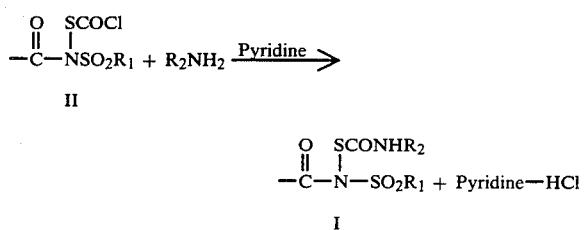

Compounds of this invention having Formula I in which Z is $R_2CH=N-O$ or $(R_2)_2C=N-O$ can be easily prepared, by reacting one mole equivalent of the alkali metal salt of the appropriate aldehyde oxime ($R_2CH=NOH$) or the appropriate ketone oxime ($R_2C=NOH$) with the appropriate intermediate II, synthesized as described above. The alkali salt of the oxime can be added to the intermediate II as anhydrous solid dispersed or dissolved in tetrahydrofuran or dialkyl ether or dichloromethane, etc. The addition of the oxime salt can be completed in about 30 minutes to about one hour, at room temperature, or lower, while stirring. The reaction mixture can be stirred for an additional one hour to about 12 hours, preferably for about 2 hours to about 6 hours. The reaction product, having Formula I, can be separated and purified by simple procedures known to those skilled in the art of organic synthesis. The overall reaction can be illustrated as:

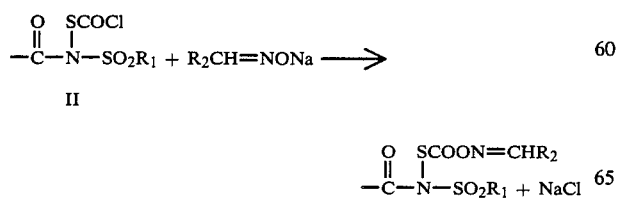

HERBICIDAL PROPERTIES & APPLICATION

The compounds of this invention having Formula I are lipophilic in properties and translocate readily in weed plants but are biochemically safe to crop plants such as soybean, peanut and cotton. Unlike the N-sulphonyl-3-phenoxybenzamide derivatives, disclosed in the published U.S. Pat. No. 4,285,723 which have an undesirable toxic carry-over effect to the crop plants growth during the subsequent season. For example there are evidences for damages occuring to winter wheat grown in soybean fields previously treated with the above mentioned herbicides. The herbicides of this invention having Formula I are expected to have no carry-over toxic effect because of their relatively rapid degradation in the soil. The compounds of this invention can be advantageously employed as herbicides and various crops for example, soybeans, cotton, and peanuts. They can be applied per se, but may be applied as the toxic components is pesticidal compositions of the compound and a carrier. These compositions may be applied directly to the soil and often incorporated therewith. The compositions can can be applied as granulars or dusts; as liquid sprays, or as gas-propelled sprays and can contain, in addition to a carrier, additiives such as emulsifying agents, binding agents gases compressed to the liquid state, odorants, stabilizers, and the like. A wide variety of liquid and solid carriers including talc, bentonite, diatomaceous earth pyrophyllite, fuller earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice herbicidal application is measured in terms of pounds of herbicide applied per acre. The compounds of this invention are effective herbicides when applied in herbicidal amounts, e.g., at rates between about 0.03 pound and about 10 pounds per acre.

EXAMPLE I

This example illustrates the improved method of preparation of the precursor, 5-(2-chloro-4-trifluoromethylphenoxy)-2-nitrobenzoic acid sulphonamides.

5-(2-chloro-4-trifluoromethylphenoxy)-2-nitrobenzoic acid (2 gm) is heated under reflux in excess of thionyl chloride (20 ml) for 90 minutes. The excess thionyl chloride is removed under vacuum. The residual product is mixed with at least 1.5 mole equivalent $CH_3SO_2NH_2$, heated slowly in an oil bath to about 110° C. The reaction temperature is slowly raised to about 150° C. and kept at that temperature for at least 30 minutes or till the HCl ceases to evolve. The reaction mixture is cooled and the residue is crystallized from isopropanol to give 5-(2chloro-4-trifluoromethylphenoxy)-2-nitro-N-methansulphonyl benzamide, m.p. 201° C. In a similar way, but using the appropriate sulphonamide in place of methanesulphonamide, the corresponding nitrobenzoic acid sulphonamides are obtained, giving the following melting points 162° C., 179° C., 185° C., 170° C., 101° C., from the reaction with ethyl, propyl, butyl, hexyl and trifluoromethanesulphonamide respectively.

EXAMPLE II

This example illustrates the preparation of the precursor-intermediates II.

The potassium salt of 5-(2-chloro-4-trifluoromethylphenoxy)-2-nitro-N-methanesulphonyl benzamide, 0.05 mole, in about 100 ml tetrahydrofuran is cooled to about 0° C. carbonylsulfide dichloride ClSCOCl, 0.05 mole dissolved in dichloromethane, is added slowly over a period of 60 minutes while stirring. Stirring is continued for additional 2 hours. The reaction product

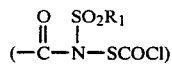

is used in the same reaction mixture, without isolation, to prepare the various compounds of this invention.

In a similar way the above procedure can be used to prepare other precursor-intermediate II

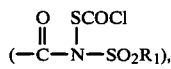

such as those having $R_1$ as $C_2H_5$, $C_3H_7$, $C_4H_9$, $C_6H_{13}$ or $CF_3$.

EXAMPLE III

This example illustrates the preparation of compounds of Formula I wherein Z is $OR_2$ or $SR_2$.

The N-sulfenylcarbonylchloride-5-(2-chloro-4-trifluoromethylphenoxy)-2-nitro-N-methane-sulphonyl benzamide, prepared and kept in the reaction solvent as described in Example II, 0.05 mole, is reacted with $CH_3ONa$, 0.05 mole, dissolved in methanol, 20 ml. The $CH_3ONa$-methanol solution is added slowly at room temperature, while stirring, over a period of about 30 minutes, and then stirring is continued for an additional 3 hours. Solvent is evaporated under vacuum, the residual product is washed with cold water, dried and crystallized from methanol. The product is characterized as N-carboxymethylsulfenyl-5-(2-chloro-4-trifluoromethylphenoxy)-2-nitro-N-methanesulphonyl benzamide. In a similar way, but using the sodium salt of the appropriate alcohol, mercaptan, phenol or thiophenol in place of $CH_3ONa$, the corresponding products of Formula I in which Z is $OR_2$ or $SR_2$ and $R_1$ is methyl can be obtained in good yields. Examples of the alcohols, mercaptans, phenols and thiophenols that can be used, utilizing the above procedure include: $C_2H_5OH$, $C_4H_9OH$, cyclohexanol, benzyl alcohol, propargy alcohol, furfuryl alcohol, ethylene glycol, propylene glycol; methyl, ethyl, propyl or butyl mercaptan, $HS—CH_2CH_2OH$, $HS—CH_2—CH_2—SH$, $HS—CH_2—CH_2—S—$alky ($C_1$-$C_4$), furfuryl mercaptan, $HS—CH_2COO$-alky ($C_1$-$C_4$); phenol, halogen-substituted phenol, etc.; thiophenol, halogen and/or carboxymethyl-substituted phenol, etc.

EXAMPLE IV

This example illustrates the preparation of compounds of Formula I, in which Z is $NH_2$, $NHR_2$ or $N(R_2)_2$.

The N-sulfenylcarbonylchloride-5-(2chloro-4-trifluoromethylphenoxy)-2nitro-N-methane-sulphonyl benzamide prepared in solution as in Example II, 0.05 mole is reacted with anhydrous ammonia, 0.1 mole dissolved in tetrahydrofuran cooled at 0° C. The ammonia solution is added dropwise, while stirring, to the N-sulfenyl-carbony chloride (intermediate II) over a period of one hour. The reaction mixture is stirred for an additional 6 hours, then the solvent is removed under vacuum. The residual product is dissolved in ether, washed with cold water, dried over anhydrous sodium sulfate, filtered and evaporated. The residual product is characterized as N-sulfenylcarbonylamine-5-(2-chloro-4-trifluoromethylphenoxy)-2-nitro-N-methanesulphonyl benzamide. The reaction product is suitable for use, without further purification, in a herbicidal composition, as hereinafter described. If desired, the reaction product can be crystallized from methanol. In a similar way but using an appropriate amine in place of the ammonia, the corresponding N-sulfenylcarbonylamine can be obtained in good yields. Examples of the amines that can be used utilizing the above procedure, include: ($C_1$-$C_5$)-alkylamine, ethanolamine, benzylamine, furfurylamine, aniline, ($C_1$-$C_5$)-dialkylamine, diethanolamine, etc.

EXAMPLE V

This example illustrates the preparation of compounds of Formula I, in which Z is $R_2$—CH=N—O or $(R_2)_2$—C=N—O.

The N-sulfenylcarbonyl-chloride-5-(2 chloro-4-trifluoromethylphenoxy)-2-nitro-N-methanesulphonyl benzamide, prepared in solution as in Example II, 0.05 mole is reacted with 0.055 mole of the potassium salt of acetaldoxime in tetrahydrofuran, at room temperature. The reaction mixture is stirred over night, (16 hours), then the solvent is evaporated under vacuum and the residual product is dissolved in dichloromethane, washed with water, dried over anhydrous sodium sulfate, filtered and evaporated.

The residual product can be crystallized from ethanol and is characterized as N-sulfenylcarboxy-(ethyl)-imine-5-(2chloro-4-trifluoromethylphenoxy)-2-nitro-N-methanesulphonamide. In a similar way, but using an appropriate oxime in place of acetaldoxime (acetaldehyde oxime), the corresponding N-sulfenylcarboxyimine derivatives can be obtained in satisfactory yields. Oximes that can be used utilizing the above procedure, include, ($C_2$-$C_6$)-aldehyde oxime, cyclohexanone oxime, furfural oxime, acetone oxime, benzaldehyde oxime, acetophenone oxime, etc.

Examples of Applications

EXAMPLE VI

An emulsifiable concentrate is composed of 10 parts by weight of each of the reaction products obtained from Examples III, IV and V, 75 parts by weight of dichlormethane as a solvent, 10 parts by weight nonylphenol (10 EO), as emulsifier, and 5 parts by weight of Tween 20(a trade mark for a surface active agent.

EXAMPLE VII

A mixture of weeds and some crops are sown in vessels having a diameter of 29×22×6 cm. Charged with earth and the seeds are covered with earth. The vessels are watered and kept outdoors during the Summer Growing Season. One week after the crop plants and the weeds have emerged, a herbicidal composition from Example VI, is emulsified in water and sprayed (post-emergence-test) on to the young weed and crop plants at a rate equivalent to about 500 liters per acre. Damage to the plants is assessed 14 days after spraying by comparison with untreated plants, on a scale of 0 to 10 where 0 is 0 to 10% damage and 10 is complete kill. Representative results of the test are shown in table 1.

A test is also carried out to detect preemergence herbicidal activity. Seeds of the test plant species are sown in vessels charged with earth, and the seeds were covered with earth. A herbicidal composition from Example VI, emulsified in water, is sprayed on the surface of the soil, at a rate equivalent to about 500 liters per acre. Damage to the plants is assessed 21 days after spraying by comparison with untreated soil. Representative results of the test are shown in table 1.

VIII, which has been emulsified in water is sprayed on the surface of the soil (pre-emergence test), at a rate equivalent to about 500 liters per acre. Damage to the plants is assessed 21 days after spraying, by comparison with untreated soil. The results show that the products of this invention have very good herbicidal activity against broad leaf weeds and grasses when applied at the rate lb/acre, or less, and simultaneously there is excellent preserving effect of the crop plants, including

TABLE 1

| Compound $X_1 = Cl, X_2 = CF_3, X_3 = NO_2$ | | Rate of Application | Test Plants (post-emergence) | | | | | | | |
|---|---|---|---|---|---|---|---|---|---|---|
| $R_1$ | Z | lb/acre | CG | BYG | PW | VL | CB | MG | CN | SB |
| $CH_3$ | $OCH_3$ | 0.5 | 10 | 7 | 10 | 10 | 9 | 9 | 0 | 1 |
| $CH_3$ | $OCH_3$ | 0.25 | 9 | 4 | 9 | 9 | 8 | 9 | 0 | 0 |
| $CH_3$ | $OCH_2CH_2OH$ | 0.5 | 9 | 6 | 9 | 9 | 9 | 8 | 0 | 1 |
| $CH_3$ | $OCH_2CH_2OH$ | 0.25 | 6 | 5 | 9 | 8 | 7 | 7 | 1 | 0 |
| $CH_3$ | $SCH_3$ | 0.5 | 9 | 8 | 10 | 9 | 8 | 8 | 1 | 2 |
| $CH_3$ | $SCH_3$ | 0.25 | 8 | 7 | 10 | 7 | 7 | 7 | 1 | 1 |
| $CH_3$ | $S-CH_2CH_2OH$ | 0.5 | 10 | 9 | 10 | 9 | 8 | 9 | 1 | 1 |
| $CH_3$ | $S-C_6H_5$ | 0.5 | 8 | 6 | 10 | 9 | 8 | 7 | 2 | 1 |
| $CH_3$ | $NH_2$ | 0.5 | 10 | 8 | 10 | 9 | 9 | 9 | 0 | 0 |
| $CH_3$ | $NH_2$ | 0.25 | 8 | 3 | 10 | 8 | 9 | 8 | 0 | 0 |
| $CH_3$ | $NHC_2H_5$ | 0.5 | 10 | 7 | 10 | 9 | 8 | 9 | 1 | 0 |
| $CH_3$ | $N(C_3H_7)_2$ | 0.5 | 7 | 8 | 10 | 10 | 9 | 8 | 2 | 1 |
| $CH_3$ | $O-N=CHCH_3$ | 0.5 | 9 | 8 | 10 | 8 | 9 | 8 | 1 | 1 |
| $CH_3$ | $O-N=C(CH_3)_2$ | 0.5 | 8 | 9 | 9 | 7 | 8 | 9 | 0 | 1 |
| $CH_3$ | $O-N=CHC_6H_5$ | 0.5 | 7 | 6 | 9 | 6 | 7 | 8 | 2 | 1 |
| $CF_3$ | $OCH_3$ | 0.25 | 9 | 8 | 9 | 8 | 8 | 9 | 0 | 1 |
| $CF_3$ | $SCH_3$ | 0.25 | 10 | 7 | 10 | 9 | 8 | 7 | 1 | 0 |
| $CF_3$ | $NHC_2H_5$ | 0.25 | 9 | 7 | 9 | 9 | 9 | 8 | 2 | 1 |

| Compound $X_1 = Cl, X_2 = CF_3, X_3 = NO_2$ | | Rate of Application | Test Plants (pre-emergence) | | | | | | | | |
|---|---|---|---|---|---|---|---|---|---|---|---|
| $R_1$ | Z | lb/acre | CG | BYG | PW | VL | CB | MG | CN | SB | CT |
| $CH_3$ | $OCH_3$ | 0.5 | 9 | 7 | 10 | 8 | 8 | 7 | 3 | 1 | 3 |
| $CH_3$ | $OCH_3$ | 0.25 | 7 | 3 | 8 | 8 | 7 | 6 | 3 | 0 | 2 |
| $CH_3$ | $OCH_2CH_2OH$ | 0.5 | 8 | 7 | 9 | 8 | 8 | 7 | 3 | 1 | 3 |
| $CH_3$ | $OCH_2CH_2OH$ | 0.25 | 7 | 5 | 9 | 7 | 7 | 6 | 3 | 1 | 1 |
| $CH_3$ | $SCH_3$ | 0.5 | 9 | 7 | 10 | 9 | 8 | 8 | 4 | 1 | 3 |
| $CH_3$ | $SCH_3$ | 0.25 | 8 | 4 | 10 | 8 | 7 | 6 | 3 | 0 | 1 |
| $CH_3$ | $SCH_2CH_2SH$ | 0.5 | 9 | 8 | 10 | 9 | 8 | 5 | 4 | 1 | 3 |
| $CH_3$ | $NH_2$ | 0.5 | 9 | 8 | 9 | 9 | 8 | 7 | 3 | 0 | 2 |
| $CH_3$ | $NHCH_3$ | 0.5 | 8 | 9 | 10 | 7 | 6 | 8 | 2 | 1 | 1 |
| $Ch_3$ | $NHC_2H_5$ | 0.5 | 9 | 7 | 9 | 8 | 9 | 8 | 3 | 0 | 3 |
| $CH_3$ | $O-N=CHCH_3$ | 0.5 | 8 | 7 | 10 | 8 | 7 | 9 | 2 | 1 | 2 |
| $CH_3$ | $O-N=C(CH_3)$ | 0.5 | 7 | 6 | 10 | 9 | 8 | 6 | 3 | 1 | 2 |
| $C_2H_5$ | $OCH_3$ | 0.5 | 9 | 8 | 9 | 8 | 9 | 8 | 2 | 0 | 2 |
| $C_2H_5$ | $SCH_3$ | 0.25 | 9 | 7 | 10 | 8 | 8 | 6 | 4 | 1 | 3 |

Name of test plants in table 1:
CG Crab Grass
BYG Barnyard Grass
PW Pig Weed
VL Velvet leaf
CB Cocklebur
MG Morning Glory
CN Corn
SB Soybean
CT Cotton

EXAMPLE VIII

A wettable powder easily dispersable in water is obtained by mixing 25 parts by weight of each of the reaction products obtained from Examples III, IV and V, as active ingredients, 64 parts by weight of kaolin containing quartz as inert substance, 10 parts by weight of potassium salt of ligninsulfonic acid, 1 part by weight of sodium salt of oleyomethyltaurine as wetting and dispersing agent and by grinding it.

EXAMPLE IX

A mixture of weeds and some crop plants are sown in vessels, charged with earth and the seeds are covered with earth. A herbicidal composition from Example soybean, corn and cotton.

EXAMPLE X

Another test is also carried out to test post-emergence herbicidal activity. Seeds of the test plant species are sown and covered with earth. One week after the crop and weed plants have emerged, the herbicidal composition cited in Example VIII, is emulsified in water, is sprayed on the young weed and crop plants, at the rate of about 500 liters per acre. Damage to the plants is assessed 14 days after spraying, by comparison with untreated plants. The results show that the products of this invention have very good herbicidal activity against broad leaf weeds and grasses when applied at the rate of lb/acre, or less, and simultaneously there is excellent preserving effect of the crop plants, including soybeans, corn and cotton.

Although the present invention has been described with preferred embodiments, it is to be understood that modifications and variations may be restored to, without departing from the spirit and scope of this invention, as those skilled in the art will readily understand. Such modifications are considered to be within the purview and scope of appended claims.

I claim:

1. Compounds having herbicidal activity of the formula

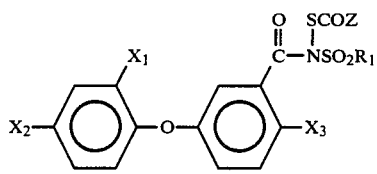

wherein:

$R_1$ is an alkyl group of 1 to 6 carbon atoms or a optionally substituted by one or more halogen atoms; phenyl group optionally substituted by one or more halogen atoms;

Z is an oxy moiety ($OR_2$); sulfenyl moiety ($SR_2$); $NH_2$; $NHR_2$; $N(R_2)_2$; $R_2CH=N-O$; $(R_2)_2CH=N-O$, and $R_2$ includes phenyl optionally substituted; heterocycle having from 5 to 7 atom rings optionally substituted; ($C_1$-$C_4$) alkyl; ($C_1$-$C_4$)alkyl optionally substituted with halogen, OH, SH, O-alkyl, S-alkyl, furfuryl, phenyl, COO alkyl, CN, or C≡CH; $X_1$ is Cl; $X_2$ is $CF_3$ and $X_3$ is $NO_2$.

2. Herbicidal compounds as claimed in claim 1 wherein $R_1$ is a methyl group; Z is a $CH_3O$ group or a $O-CH_2CH_2OH$ group.

3. Herbicidal compounds as claimed in claim 1 wherein $R_1$ is a methyl group and Z is a $CH_3S$ group or a $SCH_2CH_2OH$ group.

4. Herbicidal compounds as claimed in claim 1 wherein $R_1$ is a methyl group and Z is a $NH_2$ group or $(CH_3)_2N$ group.

5. Herbicidal compounds as claimed in claim 1 wherein $R_1$ is a methyl group and Z is a $CH_3CH=N-O$ group or a $(CH_3)_2C=N-O$ group.

6. A process of killing or severely damaging unwanted plants, which comprises applying to the plants, or to the locus thereof, a compound of Formula (I) as defined in claim 1.

7. A process of selectively controlling weeds in crops of soybean, which comprises applying, to the crop area, in an amount sufficient to control the growth of the weeds, but insufficient to damage the crop substantially, a compound of Formula (I) as defined in claim 1.

8. Herbicidal compositions, comprising as an active ingredient a compound of Formula (I) as defined in claim 1, in admixture with a carrier comprising a solid or a liquid diluent.

* * * * *